US012416618B2

(12) United States Patent
Tsai et al.

(10) Patent No.: US 12,416,618 B2
(45) Date of Patent: Sep. 16, 2025

(54) WATER QUALITY DETECTION DEVICE AND CLEANING METHOD FOR SENSOR THEREOF

(71) Applicant: INDUSTRIAL TECHNOLOGY RESEARCH INSTITUTE, Hsinchu (TW)

(72) Inventors: Tsung-Yu Tsai, Tainan (TW); Hung-Sheng Lin, New Taipei (TW); Cheng-Da Ko, Taipei (TW); Chun-Te Chuang, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 330 days.

(21) Appl. No.: 18/111,230

(22) Filed: Feb. 17, 2023

(65) Prior Publication Data

US 2024/0142428 A1 May 2, 2024

(30) Foreign Application Priority Data

Oct. 31, 2022 (TW) .................................. 111141408

(51) Int. Cl.
*G01N 27/00* (2006.01)
*G01N 1/14* (2006.01)
*G01N 33/18* (2006.01)

(52) U.S. Cl.
CPC .............. *G01N 33/18* (2013.01); *G01N 1/14* (2013.01)

(58) Field of Classification Search
CPC .......... G01N 33/18; G01N 1/14; G01N 27/00; A46B 2200/30

(Continued)

(56) References Cited

U.S. PATENT DOCUMENTS

| 6,779,383 B2 | 8/2004 | Lizotte et al. |
| 7,542,855 B2 | 6/2009 | Sihalla |

(Continued)

FOREIGN PATENT DOCUMENTS

| CN | 105618399 B | 9/2017 |
| CN | 109029311 A | 12/2018 |

(Continued)

OTHER PUBLICATIONS

Taiwanese Office Action and Search Report for corresponding Taiwanese Application No. 111141408, dated Jul. 6, 2023.

(Continued)

*Primary Examiner* — Robert R Raevis
(74) *Attorney, Agent, or Firm* — Birch, Stewart, Kolasch & Birch, LLP (57) ABSTRACT

A water quality detection device including a detection tank, a sensor, the cleaner and a processor is provided. The sensor is disposed on the detection tank and is configured to sense a to-be-detected liquid within the detection tank. The cleaner is configured to clean the sensor. The processor is electrically connected to the sensor and the cleaner and is configured to: execute an initialization procedure, which includes driving the sensor to sense the to-be-detected liquid to obtain a number of initial sensing values and calculating a threshold value according to the initial sensing values; drive the sensor to sense the to-be-detected liquid to obtain a sensing value of the to-be-detected liquid, and determine whether the sensing value of the to-be-detected liquid reaches the threshold value; drive the cleaner to operate when the sensing value of the to-be-detected liquid reaches the threshold value.

16 Claims, 10 Drawing Sheets

(58) Field of Classification Search
USPC .......... 134/18, 44–58 R, 201; 15/3, 21.1–29;
340/540, 618–621, 635; 73/1.02, 1.03,
73/865.8, 865.9, 432.1
See application file for complete search history.

(56) References Cited

U.S. PATENT DOCUMENTS

| | | | |
|---|---|---|---|
| 8,473,262 | B2 | 6/2013 | Farruggia et al. |
| 9,903,793 | B1 | 2/2018 | Meiman, Jr. |
| 2003/0062262 | A1* | 4/2003 | Mansouri ............. G01N 33/492 |
| | | | 204/400 |
| 2014/0310895 | A1 | 10/2014 | Chen |
| 2014/0379302 | A1 | 12/2014 | Park |
| 2020/0165505 | A1 | 5/2020 | Chen et al. |
| 2021/0010989 | A1 | 1/2021 | Yizhack et al. |
| 2024/0177284 | A1* | 5/2024 | Leport ................... G06T 7/194 |

FOREIGN PATENT DOCUMENTS

| | | |
|---|---|---|
| CN | 107110839 B | 4/2019 |
| CN | 210318753 U | 4/2020 |
| CN | 111595909 A | 8/2020 |
| CN | 113607905 A | 11/2021 |
| CN | 114236082 A | 3/2022 |
| TW | M582881 U | 9/2019 |
| TW | 202004180 A | 1/2020 |
| TW | M604118 U | 11/2020 |
| TW | 202238124 A | 10/2022 |

OTHER PUBLICATIONS

Taiwanese Office Action and Search Report for Taiwanese Application No. 111141408, dated Mar. 8, 2024.
Cleary et al., "Development and Deployment of a Microfluidic Platform for Water Quality Monitoring", in Smart Sensors for Real-Time Water Quality Monitoring, Heidelberg, Berlin, 2013, pp. 125-148.
Delgado et al., "Antifouling Strategies for Sensors Used in Water Monitoring: Review and Future Perspectives", Sensors 2021, vol. 21, 389, pp. 1-25.
Lizotte et al., "10 Tips to Prevent Biofouling on Water Quality Instruments", YSI, Xylem, Inc., 2013, total 8 pages.

* cited by examiner

WATER QUALITY DETECTION DEVICE AND CLEANING METHOD FOR SENSOR THEREOF

This application claims the benefit of Taiwan application Serial No. 111141408, filed Oct. 31, 2022, the subject matter of which is incorporated herein by reference.

TECHNICAL FIELD

The disclosure relates in general to a water quality detection device and a cleaning method for a sensor thereof.

BACKGROUND

After having been used over a period, most sensors of current water quality detection devices are susceptible to the deposition or attachment of impurities. For instance, if biofilm growth is not sensed and cleaned in time, sensing error will occur and the lifespan of the sensor will be affected. Since the water quality detection device normally needs to be monitored, maintained, and cleaned, extra labor is required, and the operation and maintenance cost of the water quality detection device will increase.

SUMMARY

According to one embodiment of the disclosure, a water quality detection device. The water quality detection device includes a detection tank, a sensor, a cleaner and a processor. The sensor is disposed on the detection tank and is configured to sense a to-be-detected liquid within the detection tank. The cleaner is configured to clean the sensor. The processor is electrically connected to the sensor and the cleaner and is configured to: execute an initialization procedure, which includes driving the sensor to sense the to-be-detected liquid to obtain a number of initial sensing values and calculating a threshold value according to the initial sensing values; drive the sensor to sense the to-be-detected liquid to obtain a sensing value of the to-be-detected liquid, and determine whether the sensing value of the to-be-detected liquid reaches the threshold value; drive the cleaner to operate when the sensing value of the to-be-detected liquid reaches the threshold value.

According to another embodiment of the disclosure, a cleaning method. The cleaning method is applicable to a water quality detection device, wherein the water quality detection device further includes a detection tank, a cleaner, a processor and a sensor. The cleaning method includes the following steps: executing at an initialization procedure, which includes driving the sensor to sense a to-be-detected liquid within the detection tank to obtain a plurality of initial sensing values and calculating a threshold value according to the initial sensing values; driving the sensor by the processor to sense the to-be-detected liquid to obtain a sensing value of the to-be-detected liquid, and determining by the processor whether the sensing value of the to-be-detected liquid reaches the threshold value; and driving the cleaner by the processor to operate when the sensing value of the to-be-detected liquid reaches the threshold value.

The above and other aspects of the disclosure will become better understood with regard to the following detailed description of the preferred but non-limiting embodiment (s). The following description is made with reference to the accompanying drawings.

DETAILED DESCRIPTION

Figure 1A:
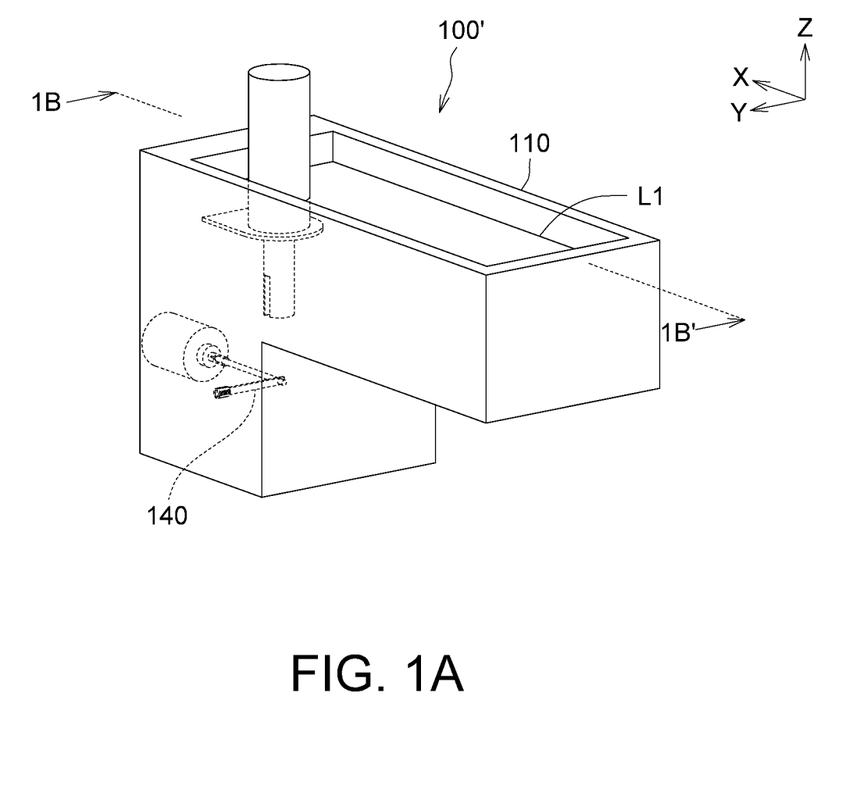
FIG. 1A is a schematic diagram of a water quality detection device according to an embodiment of the disclosure.
Figure 1B:
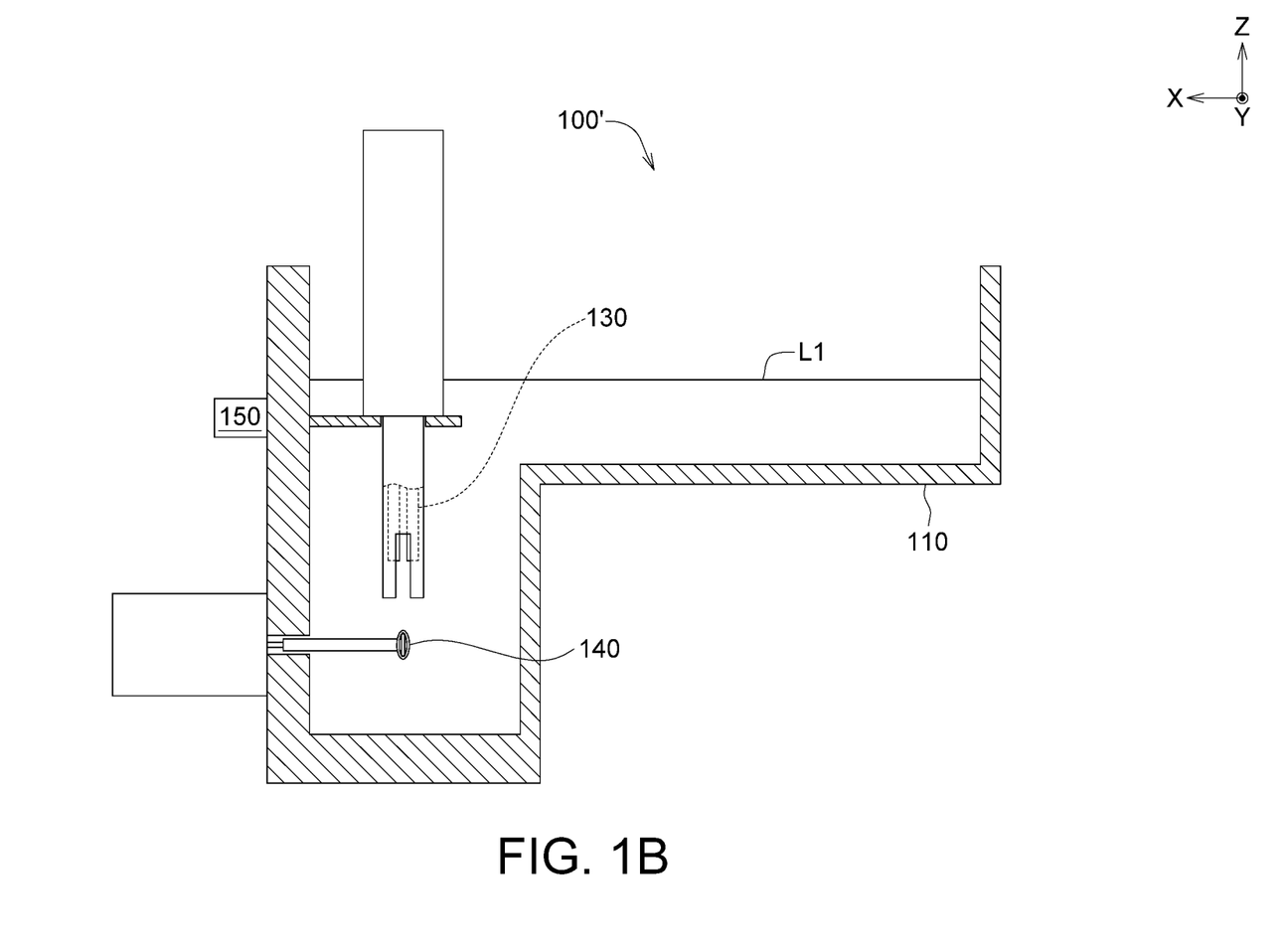
FIG. 1B is a cross-sectional view of the water quality detection device of FIG. 1A along direction 1B-16'.
Figure 1C:
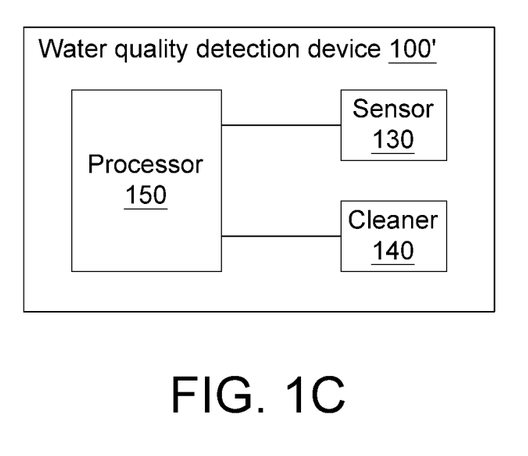
FIG. 1C is a functional block diagram of the water quality detection device of FIG. 1A.

Refer to FIGS. 1A to 1C. FIG. 1A is a schematic diagram of a water quality detection device 100' according to an embodiment of the present disclosure. FIG. 1B is a cross-sectional view of the water quality detection device 100' of FIG. 1A along direction 1B-1B'. FIG. 1C is a functional block diagram of the water quality detection device 100' of FIG. 1A.

As indicated in FIGS. 1A to 1C, the water quality detection device 100' includes a detection tank 110, a sensor 130, a cleaner 140 and a processor 150. The sensor 130 is disposed on the detection tank 110 and is configured to sense a to-be-detected liquid L1 within the detection tank 110. The cleaner 140 is configured to clean the sensor 130. The processor 150 is electrically connected to the sensor 130 and the cleaner 140 and is configured to: execute an initialization procedure, which includes driving the sensor 130 to sense the to-be-detected liquid L1' (for example, a first liquid) to obtain a number of initial sensing values R11 and calculating a threshold value R11c according to the initial sensing values R11; drive the sensor 130 to sense the to-be-detected liquid L1 (for example, a second liquid) to obtain a sensing value of the to-be-detected liquid R12 and determine whether the sensing value of the to-be-detected liquid R12 reaches a threshold value R11c; and drive the cleaner 140 to operate when the sensing value of the to-be-detected liquid R12 reaches the threshold value R11c. Thus, the water quality detection device 100' could automatically determine the cleanliness of the sensor 130 according to the sensing value of the to-be-detected liquid R12. When the sensing value of the to-be-detected liquid R12 reaches the threshold value R11c, this indicates that the cleanliness of the sensor 130 is abnormal and the accuracy of the sensing result may fail to meet the requirements. In such case, the cleaner 140 operates to clean the sensor 130. Thus, the water quality detection device 100' could sense the cleanliness of the sensor 130 and automatically clean the sensor 130 when the cleanliness of the sensor 130 is abnormal.

Figure 2A:
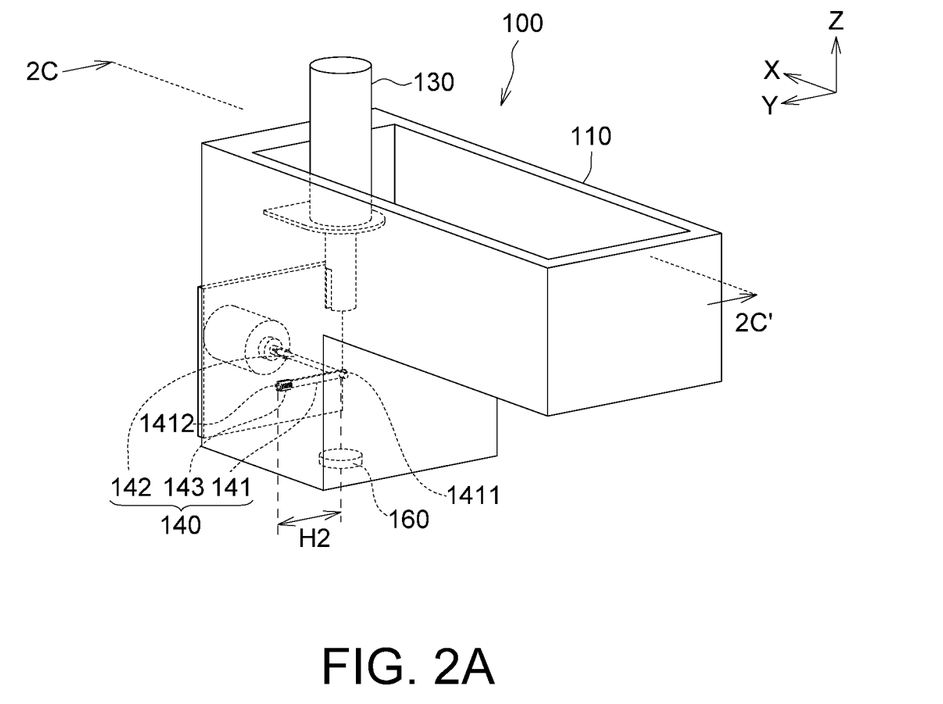
FIGS. 2A to 2B are schematic diagrams of a water quality detection device according to another embodiment of the disclosure.
Figure 2B:
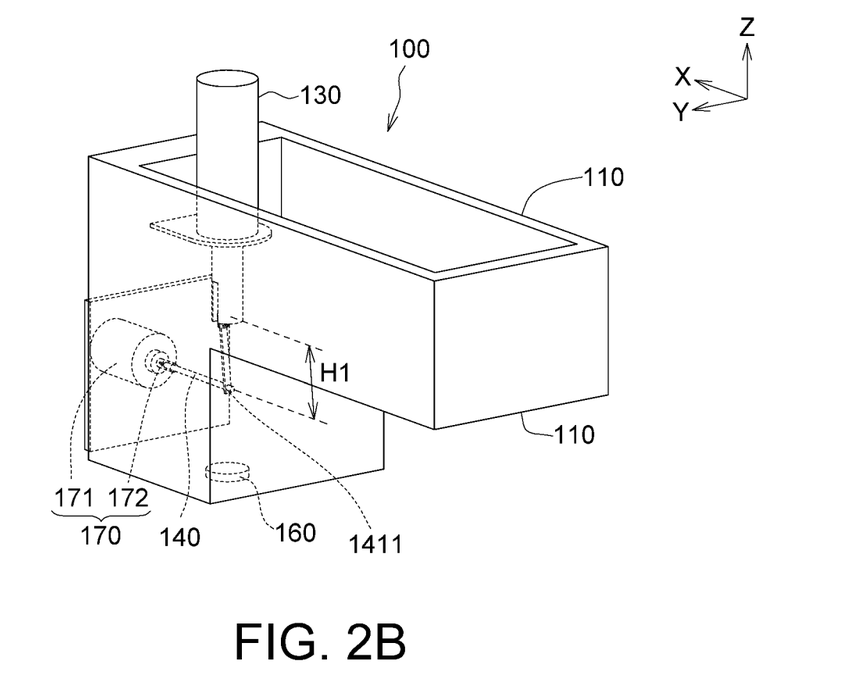
Figure 2C:
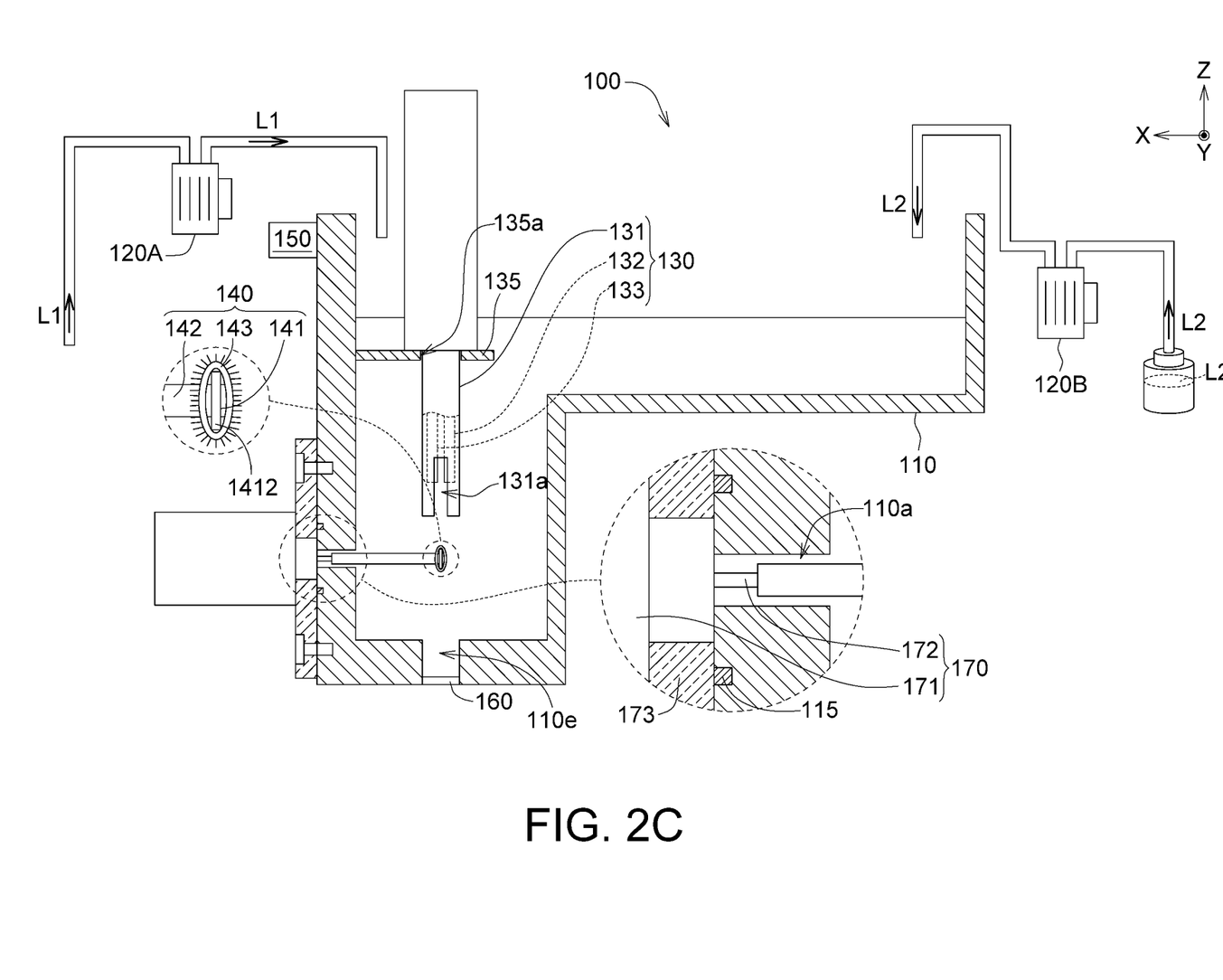
FIG. 2C is a cross-sectional view of the water quality detection device of FIG. 2A along direction 2C-2C'.
Figure 2D:
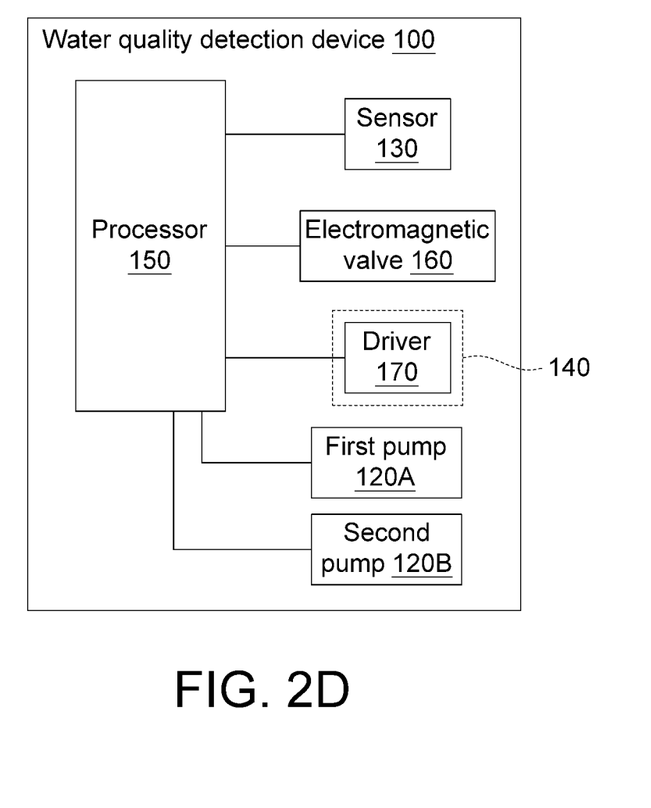
FIG. 2D is a functional block diagram of the water quality detection device of FIG. 2A.

Refer to FIGS. 2A to 2D. FIGS. 2A to 2B are schematic diagrams of a water quality detection device 100 according to another embodiment of the present disclosure. FIG. 2C is a cross-sectional view of the water quality detection device 100 of FIG. 2A along direction 2C-2C'. FIG. 2D is a schematic diagram of the water quality detection device 100 of FIG. 2A. To avoid the diagrams becoming too complicated, the first pump 120A and the second pump 120B are only illustrated in FIG. 2C and are not illustrated in FIGS. 2A to 2B.

As indicated in FIGS. 2A to 2C, the water quality detection device 100 includes a detection tank 110, a first pump 120A, a second pump 120B, a sensor 130, a cleaner 140, a processor 150, an electromagnetic valve 160. The sensor 130 is disposed on the detection tank 110 and is configured to sense the to-be-detected liquid L1 within the detection tank 110. The cleaner 140 is configured to clean the sensor 130 and includes a driver 170. The processor 150 is electrically connected to the sensor 130 and the driver 170 of the cleaner 140 and is configured to: execute an initialization procedure, which includes: driving the sensor 130 to sense the to-be-detected liquid L1' to obtain a number of initial sensing values R11 and calculating a threshold value R11c according to the initial sensing values R11; drive the sensor 130 to sense the to-be-detected liquid L1 to obtain a sensing value of the to-be-detected liquid R12, and determine whether the sensing value of the to-be-detected liquid R12 reaches the threshold value R11c; and drive the cleaner 140 to operate when the sensing value of the to-be-detected liquid R12 reaches the threshold value R11c. Thus, the water quality detection device 100 could automatically determine the cleanliness of the sensor 130 according to the sensing value of the to-be-detected liquid R12. When the sensing value of the to-be-detected liquid R12 reaches the threshold value R11c, this indicates that the cleanliness of the sensor 130 is abnormal, and the accuracy of the sensing result may fail to meet the requirements. In such case, the cleaner 140 operates to clean the sensor 130. In other words, the water quality detection device 100 could sense the cleanliness of the sensor 130 and automatically clean the sensor 130 when the cleanliness of the sensor 130 is abnormal.

The to-be-detected liquid L1 and the to-be-detected liquid L1' each has a parameter, such as conductivity, pH value, dissolved oxygen, pH, or any other parameters representing other characteristics of the to-be-detected liquid L1. For instance, when the sensor 130 is a conductivity meter, the parameter is conductivity. Diverse types of parameters have their own ways in reflecting sensor abnormalities. (1). As the cleanliness sensed by the sensor 130 turns from a normal level to an abnormal level, the sensing value of the to-be-detected liquid R12 increases to a threshold value R11c; or (2). As the cleanliness sensed by the sensor 130 turns from a normal level to an abnormal level, the sensing value of the to-be-detected liquid R12 drop to the threshold value R11c. When the sensor is an electrode sensor, the sensing value of the to-be-detected liquid R12 normally decreases to the threshold value R11c. Besides, the threshold value R11c could be a numeric value, but is not limited to a fixed value; the threshold value R11c could also be a numeric range. The to-be-detected liquid L1 could be water from a river, a reservoir, a water tower, a ditch, or a fishpond, or could be wastewater, sewage water, or discharge water.

As indicated in FIG. 2C, the first pump 120A is electrically connected to the processor 150. The first pump 120A could transport a to-be-detected liquid L1 to the detection tank 110. The detection tank 110 has a liquid discharge port 110e. The liquid within the detection tank 110 could be discharged off the detection tank 110 with the to-be-detected liquid L1 (empty the detection tank 110). The second pump 120B is electrically connected to the processor 150. The second pump 120B could transport a standard liquid L2 to the detection tank 110. Before the standard liquid L2 is transported to the detection tank 110, when there is a liquid (such as the to-be-detected liquid L2) within the detection tank 110 already, the liquid (such as the to-be-detected liquid L1) could be discharged off the detection tank 110 via the liquid discharge port 110e beforehand (empty the detection tank 110).

As indicated in FIG. 2C, the sensor 130 according to an embodiment of the present disclosure is exemplified by an electrode sensor. The sensor 130 includes a casing 131, a first sensing electrode 132 and a second sensing electrode 133, wherein the first sensing electrode 132 and the second sensing electrode 133 are disposed inside the casing 131. The casing 131 has a notch 131a, from which the first sensing electrode 132 and the second sensing electrode 133 are exposed to contact and sense the liquid within the detection tank 11, such as the to-be-detected liquid L1 or the standard liquid L2. Besides, one of the first sensing electrode 132 and the second sensing electrode 133 is a positive electrode and the other is a negative electrode. The processor 150, electrically connected to the first sensing electrode 132 and the second sensing electrode 133, receives sensing signals from the first sensing electrode 132 and the second sensing electrode 133 and analyzes or process sensing values.

As indicated in FIG. 2C, the water quality detection device 100 further includes a carrier 135. The carrier 135 is fixed on the detection tank 110 and has a through hole 135a. The casing 131 of the sensor 130 could pass through the through hole 135a and lean on the carrier 135 to fix the relative positions between the detection tank 110 and the sensor 130. In an embodiment, the carrier 135 and the casing 131 could be locked, engaged, or temporarily bonded. Since the casing 131 of the sensor 130 could pass through the through hole 135a, the first sensing electrode 132 and the second sensing electrode 133 arranged on the casing 131 face the cleaner 140 and could be cleaned thereby.

As indicated in FIGS. 2A to 2C, the cleaner 140 includes a driver 170, a first connection member 141, a second connection member 142 and a brush 143. The first connection member 141 has a first end 1411 and a second end 1412. The first connection member 141 and the second connection member 142 could be separately manufactured and then could be screwed, engaged, or soldered temporarily or permanently. Or, the first connection member 141 and the second connection member 142 could be integrally formed in one piece without leaving any boundary surface or boundary layer on the junction. The brush 143 could be disposed on the second end 1412 of the first connection member 141. One end of the second connection member 142 is connected to the first connection member 141, and the other end is connected to the driver 170. When the second connection member 142 rotates, the brush 143 connected to the first connection member 141 is driven to rotate accordingly (for instance, revolve around the X-axis) to clean the first sensing electrode 132 and the second sensing electrode 133 of the sensor 130. The brush 143 may include a number of long strings for brushing the biofilm, impurities, or oil film off the sensing electrode. The long strings could be made of animal hairs or other materials, such as metal, plastic and/or rubber. Besides, the distance H1 between the sensing electrodes (the first sensing electrode and the second sensing electrode) and the first end 1411 is equivalent to the distance H2 between the first end 1411 and the second end 1412. Thus, when the first connection member 141 rotates, the brush 143 located at the second end 1412 is driven to contact and clean the sensing electrodes.

As indicated in FIGS. 2A to 2C, the processor 150 could be realized by a physical circuit formed using a semiconductor process. The processor 150 could be electrically connected to the first pump 120A, the second pump 120B, the sensor 130, the electromagnetic valve 160, and the driver 170 of the cleaner. The processor 150 could control the first pump 120A and the second pump 120B to transport a liquid to the detection tank 110, receive the sensing signal of the sensor 130, control the driver 170 to drive the cleaner 140, and control the opening and closing of the electromagnetic valve 160.

As indicated in FIGS. 2A to 2C, the electromagnetic valve 160 is electrically connected to the processor 150. The electromagnetic valve 160, disposed on the bottom of the detection tank 110, such as at the liquid discharge port 110e on the bottom of the detection tank 110, could control the opening and closing of the liquid discharge port 110e to empty liquid and could close the bottom of the detection tank 110. When the electromagnetic valve 160 is opened, the liquid within the detection tank 110 of the detection tank 110 is discharged off the detection tank 110 via the liquid discharge port 110e and the electromagnetic valve 160; when the electromagnetic valve 160 is driven to close the liquid discharge port 110e, the bottom of the detection tank 110 could be closed to avoid the liquid within the detection tank 110 being discharged off the detection tank 110.

As indicated in FIGS. 2A to 2C, the driver 170 of the cleaner 140 includes a driving body 171 and a transmission shaft 172. The transmission shaft 172 is connected to the driving body 171, which drives the transmission shaft 172 to rotate (for instance, rotate around the X-axis). The second connection member 142 of the cleaner 140 is connected to the transmission shaft 172, wherein one end of the second connection member 142 of the cleaner 140 is connected to the transmission shaft 172 of the driver 170. The second connection member 142 could be connected to the transmission shaft 172 of the driver 170, so that the second connection member 142 could be driven by the driver 170 to rotate (for instance, rotate around the X-axis). Besides, the driving body 171, being a waterproof driving module, could avoid the liquid within the detection tank 110 being discharged off the driving body 171. In an embodiment, the driver 170 could be realized by a motor.

As indicated in FIGS. 2A to 2C, the water quality detection device 100 further includes an adapter 173; the driving body 171 is fixed on the adapter 173 and is therefore fixed on the detection tank 110 with the adapter 173. The adapter 173 and the detection tank 110 could be screwed, engaged, or soldered temporarily or permanently. The transmission shaft 172 is protruded from the adapter 173 and faces the detection tank 110. The detection tank 110 has a through hole 110a interconnected with the detection tank 110. The through hole 110a allows the transmission shaft 172 to pass through, so that the cleaner 140 could be connected to the transmission shaft 172 within the detection tank 110. During the assembly, firstly the adapter 173 could be arranged within the detection tank 110, then the driver 170 of the cleaner 140 is arranged within the adapter 173, wherein the transmission shaft 172 of the driver 170 passes through the through hole 110a of the detection tank 110 to enter the detection tank 110, then the second connection member 142 of the cleaner 140 is connected to the transmission shaft 172. Besides, the water quality detection device 100 further includes a sealing member 115, which could be interposed between the adapter 173 and the detection tank 110 to stop the liquid within the detection tank 110 leaking via the gap (if any) between the adapter 173 and the detection tank 110.

Details of the cleaning method for the water quality detection device 100' according to an embodiment of the present disclosure are disclosed below.

Figure 3:
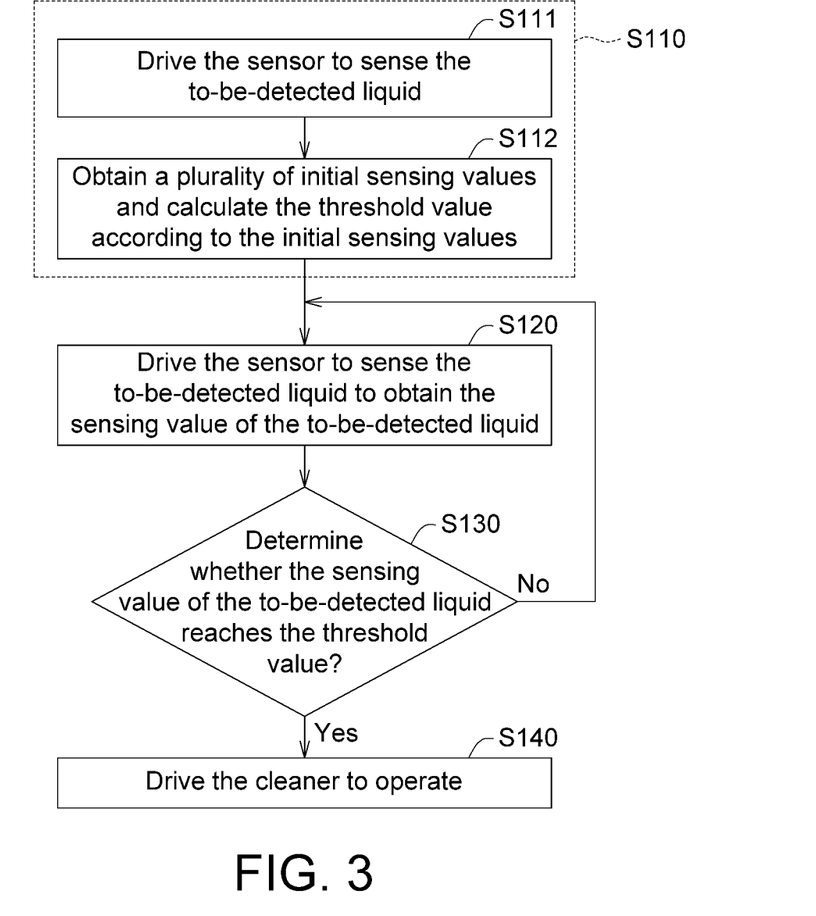
FIG. 3 is a flowchart of a cleaning method for the water quality detection device of FIG. 1A.

Refer to FIG. 3, a flowchart of a cleaning method for the water quality detection device 100' of FIG. 1A is shown.

In step S110, an initialization procedure is executed by the processor 150. At the initialization procedure, the processor 150 drives the sensor 130 to sense the to-be-detected liquid L1' within the detection tank 110 to obtain a number of initial sensing values R11 (step S111), and calculates the threshold value R11c according to the initial sensing values R11 (step S112).

In step S120, the processor 150 drives the sensor 130 to perform sensing on the to-be-detected liquid L1 to obtain a sensing value of the to-be-detected liquid R12.

In step S130, the processor 150 determines whether the sensing value of the to-be-detected liquid R12 reaches the threshold value R11c. When the sensing value of the to-be-detected liquid R12 reaches the threshold value R11c, the method proceeds to step S140. When the sensing value of the to-be-detected liquid R12 does not reach the threshold value R11c, the method returns to step S120.

In step S140, the processor 150 drives the cleaner 140 to operate.

Details of the cleaning method for the water quality detection device 100 according to an embodiment of the present disclosure are disclosed below.

Figure 4A:
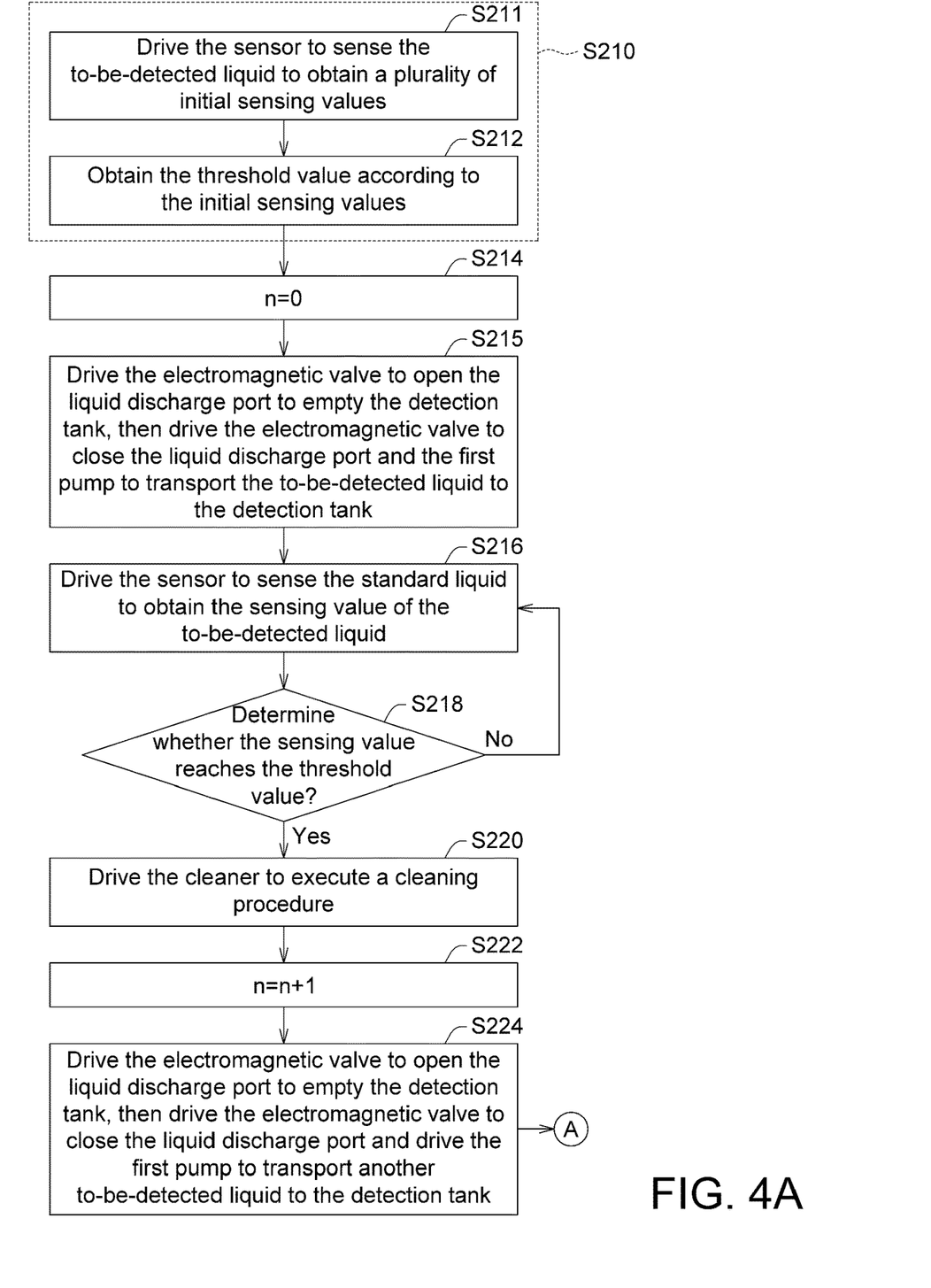
FIGS. 4A to 4B are flowchart of a cleaning method for the water quality detection device of FIG. 2A.
Figure 4B:
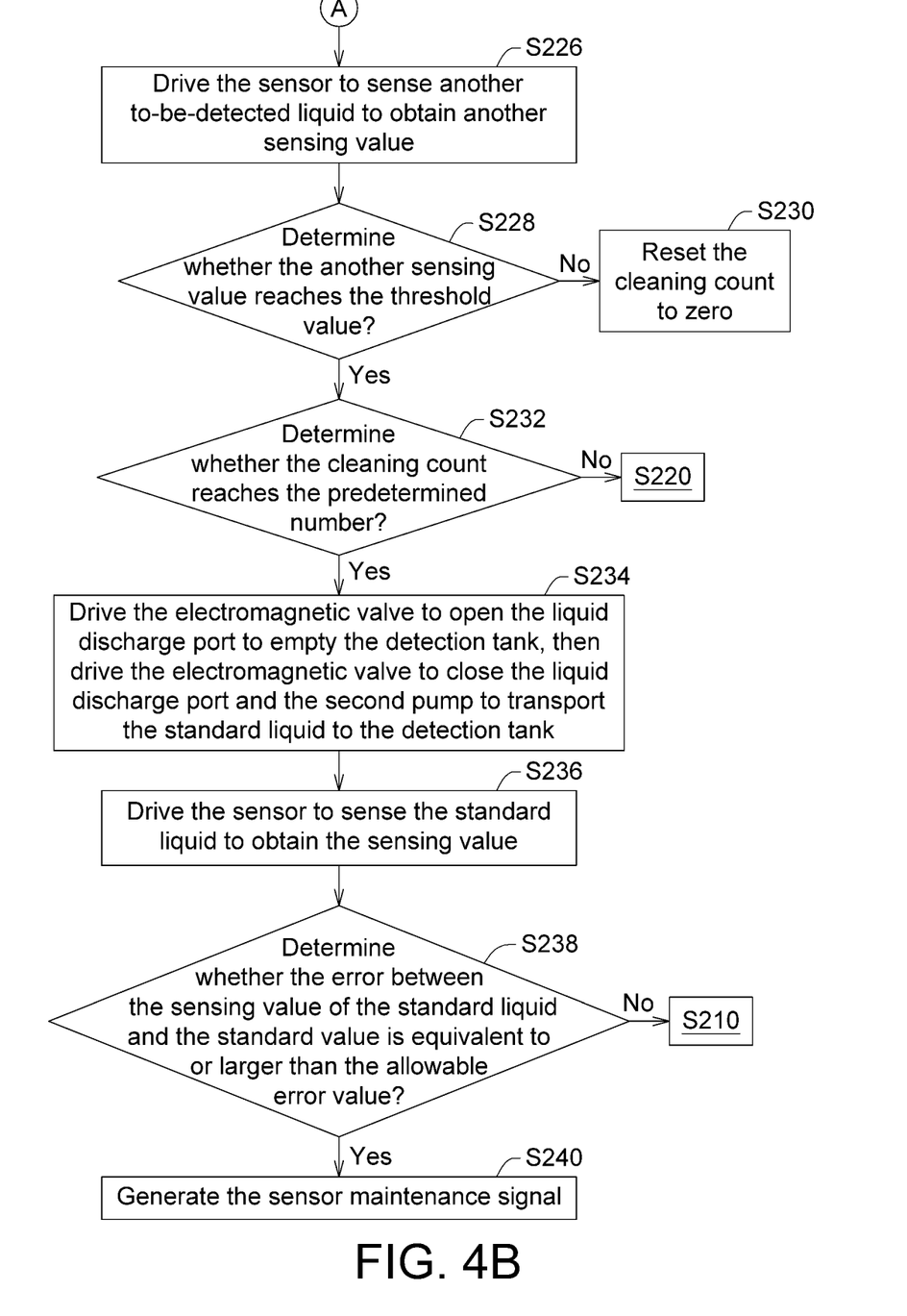
Figure 5:
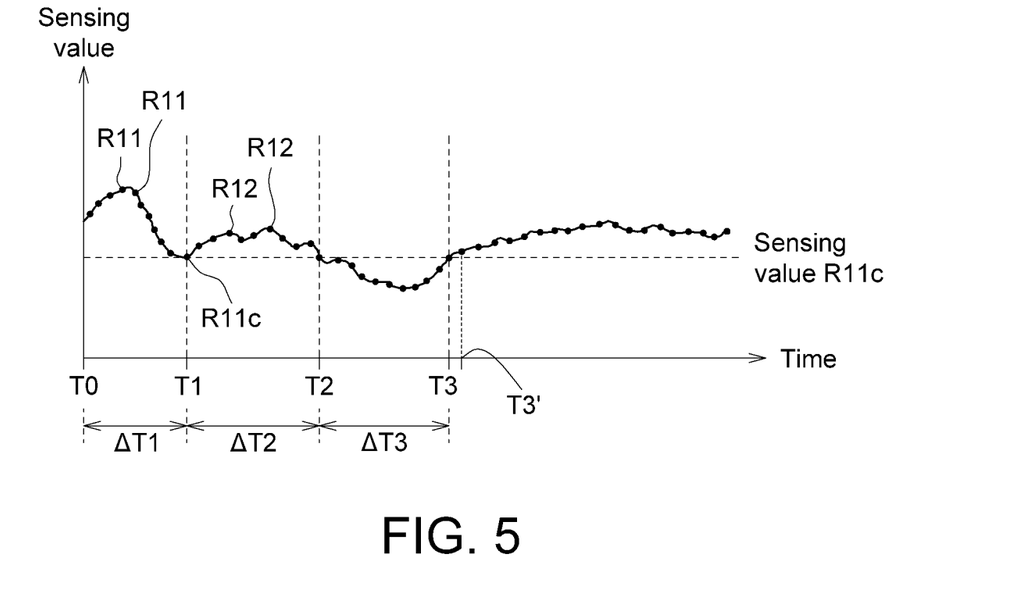
FIG. 5 is a relationship diagram of sensing value vs time for the sensor of FIG. 2A.

Refer to FIGS. 4A to 4B and 5. FIGS. 4A to 4B are flowcharts of a cleaning method for the water quality detection device 100 of FIG. 2A. FIG. 5 is a relationship diagram of sensing value vs time for the sensor 130 of FIG. 2A.

Firstly, the method begins at step S210, an initialization procedure including steps S211 to S212 is executed by the processor 150.

As indicated in FIG. 5, time interval ΔT1 (for instance, a number of hours to a number of days) between time points T0 to T1 is the duration of executing step S211 of the initialization procedure. In step S211, the sensor 130 performs sensing on the to-be-detected liquid L1' to obtain a number of initial sensing values R11. The number of items of initial sensing values R11 depends on the sampling time. For instance, all the sensing values obtained by the sensor 130 during the time interval ΔT1 between time points T0 to T1 belong to initial sensing values R11. Or, the number of items of initial sensing values R11 is a predetermined number (for instance, tens to hundreds), and the length of the time interval ΔT1 depends on the predetermined number or the sensing frequency.

Each item of initial sensing values R11 is the sensing value of a renewed to-be-detected liquid L1'. In other words, to obtain each item of initial sensing values R11, the processor 150 opens the electromagnetic valve 160 to discharge the to-be-detected liquid L1' that has been detected (to empty the detection tank 110), then drives the electromagnetic valve 160 to close the liquid discharge port 110e and drives the first pump 120A to transport the to-be-detected liquid L1' to the detection tank 110, that is, to renew the to-be-detected liquid L1' within the detection tank 110. After the to-be-detected liquid L1' is renewed, the processor 150 drives the sensor 130 to sense the to-be-detected liquid L1' to obtain an item of initial sensing values R11. By the same analogy, the sensor 130 could obtain several items of initial sensing values R11.

In step S212, the processor 150 obtains a threshold value R11c of the initial sensing values R11 according to the initial sensing values R11. In a situation, the threshold value R11c is where the cleanliness of the sensing electrode of the sensor 130 turns from a normal level to an abnormal level. As the cleanliness of the sensing electrode turns from a normal level to an abnormal level, when the initial sensing value R11 decreases, the threshold value R11c could be the minimum of the initial sensing values R11 or a value lower than the average value of the initial sensing values R11. In another situation, as the cleanliness of the sensing electrode turns from a normal level to an abnormal level, when the initial sensing values R11 increase, the threshold value R11c could be the maximum of the initial sensing values R11 or a value higher than the average of the initial sensing values R11.

In the embodiment, as indicated in FIG. 5, the threshold value R11c is the minimum of the initial sensing values R11 (such as a sensing value within the time interval ΔT1).

After executing the initialization procedure to obtain the threshold value R11c, the processor 150 then executes a measurement procedure, which includes steps S214 to S218. In the embodiment, as indicated in FIG. 5, the time interval ΔT2 between time points T1 to T2 is the period of steps S214 to S218.

In step S214, the initial value of the cleaning count n is exemplarily set to 0 by the processor 150.

In step S215, the processor 150 drives the electromagnetic valve 160 to open the liquid discharge port 110e to empty the detection tank 110, then drives the electromagnetic valve 160 to close the liquid discharge port 110e, and the first pump 120A to transport the to-be-detected liquid L1 to the detection tank 110.

In step S216, the sensor 130 is driven by the processor 150 to sense the to-be-detected liquid L1 to obtain a sensing value of the to-be-detected liquid R12.

In step S218, the processor 150 determines whether the sensing value of the to-be-detected liquid R12 reaches the threshold value R11c. When the processor 150 determines that the sensing value of the to-be-detected liquid R12 does not reach the threshold value R11c, the method proceeds to step S216. In step S216, the sensor 130 is driven to sense the next preparation of to-be-detected liquid L1 to obtain the next sensing value of the to-be-detected liquid R12. By the same analogy, the processor 150 could obtain several sensing values of the to-be-detected liquid R12 via the sensor 130.

Each sensing value of the to-be-detected liquid R12 is the sensing value of a renewed to-be-detected liquid L1 within the detection tank 110. To put it in greater details, before the next sensing value of the to-be-detected liquid R12 is obtained, the processor 150 opens the electromagnetic valve 160 to discharge the to-be-detected liquid L1 within the detection tank 110 that has been detected, that is, to empty the detection tank 110, then closes the electromagnetic valve 160. Then the processor 150 drives the first pump 120A to transport the to-be-detected liquid L1 to the detection tank 110 and drives the sensor 130 to sense the renewed to-be-detected liquid L1 to obtain the next sensing value of the to-be-detected liquid R12.

On the other hand, when the processor 150 determines that the sensing value of the to-be-detected liquid R12 reaches the threshold value R11c, the processor 150 executes steps S220 to S232. As indicated in FIG. 5, the time interval ΔT3 between time points T2 to T3 is the period of steps S220 to S232.

In step S220, the processor 150 drives the cleaner 140 to execute a cleaning procedure for cleaning the sensor 130. As indicated in FIGS. 2A to 2B, the processor 150 controls the transmission shaft 172 of the driver 170 of the cleaner 140 to rotate, so that the first connection member 141 and the second connection member 142 of the cleaner 140 could drive the brush 143 to rotate to clean the sensing electrode of the sensor 130. The processor 150 drives the cleaner 140 to execute a cleaning procedure. At the cleaning procedure, the cleaner 140 continuously cleans the sensor 130 for a cleaning time, then stops. The cleaning time is within a range of 30 to 60 seconds.

In step S222, the cleaning count n is increased by 1 by the processor 150, for instance, n=n+1.

In step S224, the processor 150 drives the electromagnetic valve 160 to open the liquid discharge port 110e to empty the detection tank 110, then drives the electromagnetic valve 160 to close the liquid discharge port 110e and drives the first pump 120A to transport another (or the next) preparation of to-be-detected liquid L1 to the detection tank 110, that is, to renew the to-be-detected liquid L1 within the detection tank 110.

In step S226, the processor 150 drives the sensor 130 to sense the another to-be-detected liquid L1 to obtain another (or the next) sensing value of the to-be-detected liquid R12.

In step S228, the processor 150 determines whether the another sensing value of the to-be-detected liquid R12 obtained in step S226 still reaches the threshold value R11c. If so, the method proceeds to step S232. If no, this indicates that the cleanliness of the sensing electrode of the sensor 130 is already back to the normal level after cleaning (for instance, at the time point T3' of FIG. 5), then the method proceeds to step S230, the processor 150 resets the cleaning count n to zero (for instance, n=0) and the process again proceeds to step S216 to sense the next preparation of to-be-detected liquid L1. As disclosed above, before the next preparation of to-be-detected liquid L1 is sensed, the processor 150 drives the electromagnetic valve 160 to open to discharge the to-be-detected liquid L1 that has been detected, then closes the electromagnetic valve 160 and drives the first pump 120A to transport a to-be-detected liquid L1 to the detection tank 110, and drives the sensor 130 to sense the next preparation of to-be-detected liquid L1 to obtain a next sensing value of the to-be-detected liquid R12.

In step S232, the processor 150 determines whether the cleaning count n reaches the predetermined number N, that is, the processor 150 determines the number of times, denoted by n, for which the cleaner 140 cleans the sensor 130 reaches the predetermined number N. The predetermined number N is a numeric value greater than or equivalent to 1, such as any positive integer within a range of 1 to 30 or even larger. When it is determined that the cleaning count n reaches the predetermined count N, the method proceeds to step S234; when it is determined that the cleaning count n does not reach the predetermined count N, the method proceeds to step S220, the cleaner 140 again cleans the sensor 130.

When the cleaning count n reaches the predetermined number N and the sensing value of the to-be-detected liquid R12s still reaches the threshold value R11c, a sensor failure determination procedure (steps S234 to S240) is executed to determine whether the sensor 130 has failed. Under such circumstance, the cleaning of the sensor 130 does not help much to improve the cleanliness of the sensor 130 because the sensor 130 may have failed. If the sensor 130 fails, despite that the cleanliness of the sensing electrode of the sensor 130 is normal, the sensing value of the to-be-detected liquid R12 still may reach the threshold value R11c.

Details of the sensor failure determination procedure (steps S234 to S240) are disclosed below.

In step S234, the processor 150 drives the electromagnetic valve 160 to open the liquid discharge port 110e to empty the detection tank 110, then drives the electromagnetic valve 160 to close the liquid discharge port 110e and the second pump 120B to transport a standard liquid L2 to the detection tank 110.

In step S236, the processor 150 drives the sensor 130 to sense the standard liquid L2 within the detection tank 110 to obtain a sensing value R21 of the standard liquid L1, wherein the parameter of the standard liquid L2 and the parameter of the to-be-detected liquid L1 belong to the same type. For instance, when the parameter of the to-be-detected liquid L1 is conductivity, the parameter of the standard liquid L2 is also conductivity.

In step S238, the processor 150 determines whether the error between the sensing value R21 of the standard liquid L1 and the standard value R22 is equivalent to or larger than an allowable error value. When the error is not equivalent to or larger than the allowable error value, the method proceeds to step S210 (the initialization procedure), that is, the threshold value R11c is redefined; when the error is equivalent to or larger than the allowable error value, the method proceeds to step S240.

In other words, when the error between the sensing value R21 of the standard liquid L1 and the standard value R22 is not larger than the allowable error value, this indicates the result "the cleaning count n reaches the predetermined number N but the sensing value of the to-be-detected liquid R12 still reaches the threshold value R11c" is not caused by the failure of the sensor 130, that is, the sensor 130 still could be used but the threshold value R11c needs to be redefined, therefore step S210 is executed again. The "allowable error value" is in a range of 1% to 3%; however, the allowable error value could be smaller than 1% or larger than 3%.

In step S240, when the error between the sensing value R21 and the standard value R22 is lower than the allowable error value, the processor 150 generates a sensor maintenance signal S1 to prompt the user to maintain the sensor 130. When the error between the sensing value R21 and the standard value R22 is lower than the allowable error value, this indicates that the result "the cleaning count n reaches the predetermined number N but the sensing value of the to-be-detected liquid R12 still reaches the threshold value R11c" could be caused by the failure of the sensor 130, and the sensor 130 could no longer be used. Thus, the user could replace the sensor 130 according to the sensor maintenance signal S1.

To summarize, the water quality detection device and the cleaning method for a sensor thereof of the present disclosure are capable of automatically sensing the cleanliness of the sensor and automatically cleaning the sensor (self-cleaning) when the cleanliness of the sensor is abnormal, so that the labor cost of maintenance could be reduced and the sensing accuracy could last for a longer period of time.

It will be apparent to those skilled in the art that various modifications and variations could be made to the disclosed embodiments. It is intended that the specification and examples be considered as exemplary only, with a true scope of the disclosure being indicated by the following claims and their equivalents.

What is claimed is:

1. A water quality detection device, comprising:
a detection tank;
a sensor disposed on the detection tank and configured to sense a first liquid within the detection tank;
a cleaner configured to clean the sensor;
a first pump; and
a processor electrically connected to the sensor, the cleaner and the first pump, and configured to:
execute an initialization procedure, which comprises driving the sensor to sense the first liquid to obtain a plurality of initial sensing values and calculating a threshold value according to the initial sensing values;
drive the first pump to transport a second liquid to the detection tank after emptying the detection tank of the first liquid;
drive the sensor to sense the second liquid to obtain a sensing value of the second liquid, and determine whether the sensing value of the second liquid reaches the threshold value; and
drive the cleaner to operate when the sensing value of the second liquid reaches the threshold value.

2. The water quality detection device according to claim 1, further comprising an electromagnetic valve electrically connected to the processor, wherein the detection tank has a liquid discharge port, the electromagnetic valve is configured to control the opening and closing of the liquid discharge port to empty the detection tank.

3. The water quality detection device according to claim 2, further comprising a second pump electrically connected to the processor, wherein after the processor drives the cleaner to complete a cleaning procedure, the processor is further configured to:
drive the electromagnetic valve to open the liquid discharge port to empty the detection tank, and then drive the electromagnetic valve to close the liquid discharge port and the first pump to transport the second liquid to the detection tank;
drive the sensor to sense the second liquid to obtain another sensing value of the second liquid;
determine whether the another sensing value of the second liquid reaches the threshold value;
determine whether a cleaning count reaches a predetermined number when the another sensing value of the second liquid reaches the threshold value; and
when the cleaning count reaches the predetermined number, the processor:
drives the electromagnetic valve to open the liquid discharge port to empty the detection tank, and then drives the electromagnetic valve to closes the liquid discharge port and the second pump to transport a standard liquid to the detection tank;
drives the sensor to sense the standard liquid to obtain a sensing value of the standard liquid, and determines whether an error between a sensing value of the standard liquid and a standard value of the standard liquid is equivalent to or larger than an allowable error value; and
executes the initialization procedure again when the error between the sensing value of the standard liquid and the standard value is not larger than the allowable error value.

4. The water quality detection device according to claim 3, wherein the processor is further configured to:
generate a sensor maintenance signal when the error between the sensing value of the standard liquid and the standard value is equivalent to or larger than the allowable error value.

5. The water quality detection device according to claim 1, wherein the processor is further configured to:
determine whether the sensing value of the second liquid is equivalent to or lower than the threshold value; and drive the cleaner to execute a cleaning procedure when the sensing value of the second liquid is equivalent to or lower than the threshold value.

6. The water quality detection device according to claim 1, wherein the processor is configured to drive the cleaner to execute a cleaning procedure, and after the cleaning procedure is completed, the processor is further configured to:
increase a cleaning count by 1, and drive the sensor to sense the second liquid to obtain another sensing value of the second liquid;
determine whether the another sensing value of the second liquid reaches the threshold value;
determine whether the cleaning count reaches a predetermined number when the another sensing value of the second liquid reaches the threshold value; and
drive the cleaner to execute the cleaning procedure, and increase the cleaning count by 1 when the cleaning count does not reach the predetermined number.

7. The water quality detection device according to claim 6, further comprising an electromagnetic valve electrically connected to the processor, wherein the detection tank has a liquid discharge port, the electromagnetic valve is configured to control the opening and closing of the liquid discharge port to empty the detection tank, and the processor is further configured to:
drive the electromagnetic valve to open the liquid discharge port to empty the detection tank, and then drive the electromagnetic valve to close the liquid discharge port and the first pump to transport the second liquid to the detection tank before the sensor executes sensing to obtain the another sensing value of the second liquid; and
reset the cleaning count to zero when the another sensing value of the second liquid does not reach the threshold value.

8. The water quality detection device according to claim 1, wherein the cleaner comprises:
a driver comprising a transmission shaft;
a connection member having a first end and a second end, wherein the first end is connected to the driver; and
a brush disposed on the second end of the connection member.

9. The water quality detection device according to claim 8, wherein the sensor comprises a sensing electrode, and a distance between the sensing electrode and the first end is equivalent to a distance between the first end and the second end.

10. A cleaning method applicable to a water quality detection device, wherein the water quality detection device further comprises a detection tank, a cleaner, a processor, a sensor and a first pump, and the cleaning method comprises:
executing an initialization procedure, which comprises driving the sensor to sense a first liquid within the detection tank to obtain a plurality of initial sensing values and calculating a threshold value according to the initial sensing values;
drive the first pump to transport a second liquid to the detection tank after emptying the detection tank of the first liquid; and
driving the sensor by the processor to sense the second liquid to obtain a sensing value of the second liquid, and determining by the processor whether the sensing value of the second liquid reaches the threshold value;
driving the cleaner by the processor to operate when the sensing value of the second liquid reaches the threshold value.

11. The cleaning method according to claim 10, wherein the water quality detection device further comprises an electromagnetic valve electrically connected to the processor, and the detection tank has a liquid discharge port; the cleaning method further comprises:
controlling the electromagnetic valve by the processor to open the liquid discharge port to empty the detection tank.

12. The cleaning method according to claim 11, wherein the water quality detection device further comprises a second pump electrically connected to the processor; after the processor drives the cleaner to complete the cleaning procedure, the cleaning method further comprises:
driving the electromagnetic valve to open the liquid discharge port to empty the detection tank, and then driving the electromagnetic valve to close the liquid discharge port and the first pump to transport the second liquid to the detection tank by the processor;
driving the sensor by the processor to sense the second liquid to obtain another sensing value of the second liquid;
determining by the processor whether the another sensing value of the second liquid reaches the threshold value;
determining by the processor whether a cleaning count reaches a predetermined number when the another sensing value of the second liquid reaches the threshold value; and
when the cleaning count reaches the predetermined number, the cleaning method further comprises:
driving the electromagnetic valve to open the liquid discharge port to empty the detection tank, and then driving the electromagnetic valve to close the liquid discharge port and the second pump to transport a standard liquid to the detection tank by the processor;
driving the sensor to sense the standard liquid to obtain a sensing value of the standard liquid and determine by the processor whether an error between a sensing value of the standard liquid and a standard value of the standard liquid is equivalent to or larger than an allowable error value; and
executing the initialization procedure by the processor again when the error between the sensing value of the standard liquid and the standard value is not larger than the allowable error value.

13. The cleaning method according to claim 12, further comprising:
generating a sensor maintenance signal by the processor when the error between the sensing value of the standard liquid and the standard value is equivalent to or larger than the allowable error value.

14. The cleaning method according to claim 10, further comprising:
determining by the processor whether the sensing value of the second liquid is equivalent to or lower than the threshold value; and
driving the cleaner to execute a cleaning procedure by the processor when the sensing value of the second liquid is equivalent to or lower than the threshold value.

15. The cleaning method according to claim 10, further comprising:
driving the cleaner by the processor to execute a cleaning procedure;
after the cleaner completes the cleaning procedure, the cleaning method further comprises:
increasing a cleaning count by 1 and driving the sensor to sense the second liquid by the processor to obtain another sensing value of the second liquid;

determining by the processor whether the another sensing value of the second liquid reaches the threshold value;

determining by the processor whether the cleaning count reaches a predetermined number when the another sensing value of the second liquid reaches the threshold value; and driving the cleaner to execute the cleaning procedure by the processor and increasing the cleaning count by 1 when the cleaning count does not reach the predetermined number.

16. The cleaning method according to claim 15, wherein the water quality detection device further comprises an electromagnetic valve electrically connected to the processor, and the detection tank has a liquid discharge port; the cleaning method further comprises:

driving the electromagnetic valve to open the liquid discharge port to empty the detection tank, and then driving the electromagnetic valve to close the liquid discharge port and the first pump to transport the second liquid to the detection tank by the processor before the sensor executes sensing to obtain the another sensing value of the second liquid; and resetting the cleaning count to zero by the processor when the another sensing value of the second liquid does not reach the threshold value.

\* \* \* \* \*